US006190676B1

(12) United States Patent
Dubief et al.

(10) Patent No.: US 6,190,676 B1
(45) Date of Patent: *Feb. 20, 2001

(54) COMPOSITION COMPRISING A CERAMIDE AND A SULPHONIC UV SCREENING AGENT AND USE THEREOF

(75) Inventors: Claude Dubief, Le Chesnay; Daniéle Cauwet-Martin, Paris, both of (FR)

(73) Assignee: L'Oreal, Paris (FR)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/993,313

(22) Filed: Dec. 18, 1997

(30) Foreign Application Priority Data

Dec. 20, 1996 (FR) .................................................. 96 15762

(51) Int. Cl.⁷ ............................... A61K 6/00; A61K 7/00; A61K 7/06
(52) U.S. Cl. ..................... 424/401; 424/70.1; 424/70.9
(58) Field of Search ................................. 424/70.1, 70.9, 424/401, 59

(56) References Cited

U.S. PATENT DOCUMENTS 4,585,597 * 4/1986 Lang et al. ........................ 260/507 R
5,368,857 * 11/1994 Corcoran et al. ..................... 424/401
5,635,163 * 6/1997 Hansenne ............................. 424/60

FOREIGN PATENT DOCUMENTS 0 729 744    9/1996  (EP) .
2 718 960   10/1995  (FR) .
WO 95/00111  1/1995  (WO) .

OTHER PUBLICATIONS

Chemical Abstract No. 122:63969 (1994).

* cited by examiner

Primary Examiner—Thurman K. Page
Assistant Examiner—Sharon Howard
(74) Attorney, Agent, or Firm—Finnegan, Henderson, Farabow, Garrett & Dunner, L.L.P.

(57) ABSTRACT

A cosmetic hair composition comprising, in a cosmetically acceptable medium, at least one ceramide compound and at least one agent for screening out ultraviolet radiation containing at least one sulphonic acid radical. The invention also relates to a process of including a ceramide compound in a cosmetic hair composition containing a UV screening agent containing at least one sulphonic acid radical, in order to improve the fixing of the UV screening agent to the hair.

30 Claims, No Drawings

COMPOSITION COMPRISING A CERAMIDE AND A SULPHONIC UV SCREENING AGENT AND USE THEREOF

The present invention relates to the use of ceramide compounds, which can also be referred to as ceramide-type compounds, in, or for the manufacture of, a hair composition comprising at least one UV screening agent containing at least one sulphonic acid radical, this composition being intended to protect the hair.

It has been known for a long time that light, in particular ultraviolet light, degrades the cosmetic and/or mechanical properties of the hair. The hair then becomes dull, coarse and brittle. In contrast with the skin, the hair becomes lighter in colour.

Substances which make it possible to protect the hair from the degradations caused by atmospheric attacking factors, such as light and heat, have been sought in the cosmetics industry for many years.

In this perspective, it has already been proposed to use the sunscreens that are used for the photoprotection of the skin. However, the structure of the skin and of the hair is very different and the inventors have observed that most of the screening agents used in the skin compositions were not effective at protecting the hair.

It has been proposed to use UV screening agents having a sulphonic group in order to protect the mechanical properties of the hair, in French patent No. 2,627,085. However, these screening agents are typically only effective in large concentrations. At these concentrations, hair treated with these screening agents may feel coarse and charged and may be difficult to disentangle.

The aim of the present invention is to propose compositions which make it possible to protect the hair effectively against attack by UV rays while at the same time providing the hair with good softness and disentangling properties.

The inventors have found, surprisingly and unexpectedly, that the combination of a ceramide compound in a composition comprising a screening agent containing a sulphonic group makes it possible to increase the amount of screening agent applied to the hair and thereby to increase the protection. This increase in the amount applied does not lead to a decrease in the softness or disentangling properties. In contrast, the hair has very good softness and disentangling properties.

The subject of the present invention is a cosmetic hair composition comprising at least one ceramide compound and at least one UV screening agent containing at least one sulphonic acid radical.

One of the subjects of the present invention is the use of ceramide compounds in, or for the manufacture of, a hair composition comprising at least one UV screening agent containing at least one sulphonic acid radical, this composition being intended to protect the hair.

One of the subjects of the present invention is the use of a ceramide compound in a cosmetic hair composition comprising a UV screening agent containing at least one sulphonic acid radical, in order to enhance the application and/or the fixing of the UV screening agent to the hair.

According to the present invention, the term "hair use" is understood to refer to application of the composition to the hair in order to wash and/or treat it.

According to the invention, the UV screening agents containing at least one sulphonic acid radical can be, in particular, sulphonic derivatives of 3-benzylidene-2-camphor and more particularly those of formulae (I), (II), (Ill), (IV) and (V) below:

Formula (I):

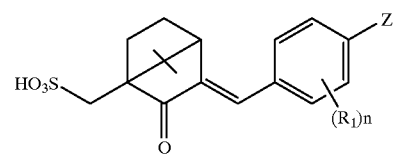

in which:
Z denotes a group

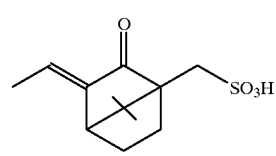

wherein
n is equal to 0 or is an integer ranging from 1 to 4 ($0 \leq n \leq 4$),
$R_1$ represents at least one, identical or different, linear or branched alkyl or alkoxy radicals containing from approximately 1 to approximately 4 carbon atoms A particularly preferred compound of formula (I) is that corresponding to n=0, namely benzene-1,4-[di(3-methylidenecamphor-10-sulphonic acid)].

Formula (II):

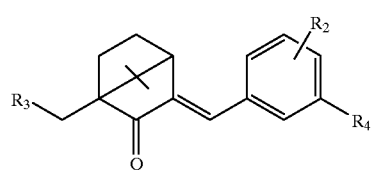

in which:
$R_2$ denotes a hydrogen atom, a halogen atom, an alkyl radical containing from approximately 1 to approximately 4 carbon atoms or an —$SO_3H$ radical,
$R_3$ and $R_4$ independently denote a hydrogen atom or an —$SO_3H$ radical, and at least one of the radicals $R_2$, $R_3$ and $R_4$ denotes the —$SO_3H$ radical.

Mention may be made, as specific examples of the compounds of formula (II), in which:
$R_2$ denotes the -$SO_3H$ radical in the para position of the benzylidenecamphor and $R_3$ and $R_4$ each denote a hydrogen atom, that is to say 4-(3-methylidenecamphor)benzenesulphonic acid.

$R_2$ and $R_4$ each denote a hydrogen atom and $R_3$ denotes an —$SO_3H$ radical, that is to say 3-benzylidenecamphor-10-sulphonic acid.

$R_2$ denotes a methyl radical in the para position of the benzylidenecamphor, $R_4$ denotes an -$SO_3H$ radical and $R_3$ denotes a hydrogen atom, that is to say 2-methyl-5-(3-methylidenecamphor)benzenesulphonic acid.

$R_2$ denotes a chlorine atom in the para position of the benzylidenecamphor,
$R_4$ denotes an —$SO_3H$ radical and $R_3$ denotes a hydrogen atom, that is to say 2-chloro-5-(3-methylidenecamphor) benzenesulphonic acid.

$R_2$ denotes a methyl radical in the para position of the benzylidene camphor, $R_4$ denotes a hydrogen atom and $R_3$ denotes an -SO₃H radical, that is to say 3-(4-methyl) benzylidenecamphor-1 0-sulphonic acid.

Formula (Ill):

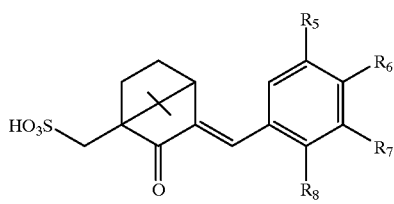

in which:

R₅ and R₇ independently denote a hydrogen atom, a hydroxyl radical, a linear or branched alkyl or alkoxy radical containing from approximately 1 to approximately 8 carbon atoms, wherein at least one of the radicals R₅ and R₇ represent a hydroxyl, alkyl or alkoxy radical, R₆ and R₈ independently denote a hydrogen atom or hydroxyl radical, wherein at least one of the radicals R₆ and R₈ denote a hydroxyl radical.

Mention may be made of specific examples of the compounds of formula (III), in which:

R₅ is a methyl radical, R₆ is a hydrogen atom, R₇ is a tert-butyl radical and R₈ is a hydroxyl radical, that is to say (3-t-butyl-2-hydroxy- 5-methyl) benzylidenecamphor-10-sulphonic acid.

R₅ is a methoxy radical, R₆ is a hydrogen atom, R₇ is a tert-butyl radical and R₈ is a hydroxyl radical, that is to say (3-t-butyl-2-hydroxy-5-methoxy) benzylidenecamphor-10-sulphonic acid.

R₅ and R₇ each denote a tert-butyl radical, R₆ denotes a hydroxyl radical and R₈ denotes a hydrogen atom, that is to say (3,5-di-tert-butyl-4-hydroxy) benzylidenecamphor-10-sulphonic acid.

Formula (IV);

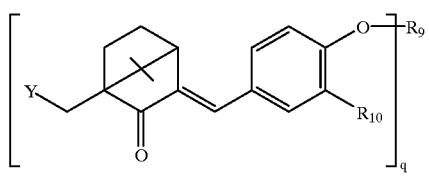

in which:

R₉ denotes a hydrogen atom, a linear or branched alkyl radical containing from approximately 1 to approximately 18 carbon atoms, a linear or branched alkenyl radical containing from approximately 3 to approximately 18 carbon atoms, a group

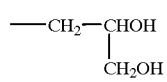

or —(CH₂CH₂O)ₙ-H, or —CH₂-CHOH-CH₃ or alternatively a divalent radical: —(CH₂)ₘ— or —CH₂-CHOH-CH₂—, n denotes an integer ranging from 1 to 6 (1≦n≦6) and m denotes an integer ranging from 1 to 10 (1≦m≦10), R₁₀ denotes a hydrogen atom, an alkoxy radical containing from approximately 1 to approximately 4 carbon atoms or a divalent radical —O— connected to the radical R₉ when the latter is also divalent, q denotes an integer equal to 1 or 2, it being understood that if q is equal to 2, R₉ must denote a divalent radical, Y and Y' independently denote a hydrogen atom or an —SO₃H radical, at least one of these radicals Y and Y' being an —SO₃H radical.

Mention may be made, as specific examples of the compounds of formula (IV), in which:

q is equal to 1, Y and R₁₀ each denote a hydrogen atom, R₉ denotes a methyl radical and Y' in position 3 denotes an —SO₃H radical, that is to say 2-methoxy-5-(3-methylidenecamphor)benzenesulphonic acid.

q is equal to 1, Y denotes an —SO₃H radical, Y' denotes a hydrogen atom and R₁₀ denotes a divalent radical —O— connected to R₉ denoting a methylene radical, that is to say 3-(4,5-methylenedioxy)benzylidenecamphor-10-sulphonic acid.

q is equal to 1, Y denotes an —SO₃H radical, Y' and R₁₀ both denote a hydrogen atom and R₉ denotes a methyl radical, that is to say 3(-4-methoxy)benzylidenecamphor-10-sulphonic acid.

q is equal to 1, Y denotes an —SO₃H radical, Y' denotes a hydrogen atom, R₉ denotes a methyl radical and R₁₀ denotes a methoxy radical, that is to say 3-(4,5-dimethoxy) benzylidenecamphor-10-sulphonic acid.

q is equal to 1, Y denotes an —SO₃H radical, Y' and R₁₀ both denote a hydrogen atom and R₉ denotes an n-butyl radical, that is to say 3-(4-n-butoxy)benzylidenecamphor-10-sulphonic acid.

q is equal to 1, Y denotes an —SO₃H radical, Y' denotes a hydrogen atom, R₉ denotes an n-butyl radical and R₁₀ denotes a methoxy radical, that is to say 3-(4-n-butoxy-5-methoxy)benzylidenecamphor-10-sulphonic acid.

Formula (V):

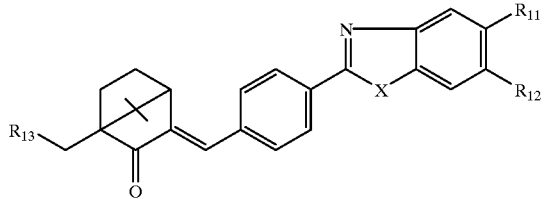

in which:

R₁₁ denotes a hydrogen atom, a linear or branched alkyl or alkoxy radical containing from approximately 1 to approximately 6 carbon atoms or an —SO₃H radical, R₁₂ denotes a hydrogen atom or a linear or branched alkyl or alkoxy radical containing from approximately 1 to approximately 6 carbon atoms, R₁₃ denotes a hydrogen atom or an —SO₃H radical, wherein at least one of the radicals R₁₁ and R₁₃ denotes an —SO₃H radical, X is an oxygen or sulphur atom or a group —NR—, wherein R is a hydrogen atom or a linear or branched alkyl radical containing from approximately 1 to approximately 6 carbon atoms.

Mention may be made, as a specific example of formula (V), of the compound in which X denotes an —NH-radical, R₁₁ denotes an —SO₃H radical and R₁₂ and R₁₃ both denote a hydrogen atom, that is to say 2-[4-(camphormethylidene) phenyl]benzimidazole-5-sulphonic acid.

The compounds of formulae (I), (II), (Ill), (IV) and (V) above are described, respectively, in U.S. Pat. No. 4,585,597 and French patent applications FR 2,236,515, 2,282,426, 2,645,148, 2,430,938 and 2,592,380, the disclosures of which are specifically incorporated by reference herein.

The screening agent containing a sulphonic group can also be a sulphonic derivative of benzophenone of formula (VI) below:

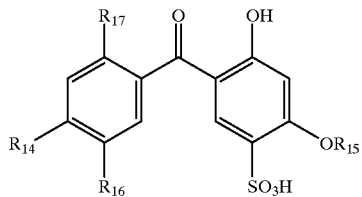

(VI)

in which:

$R_{14}$ denotes a hydrogen atom or a linear or branched alkoxy radical containing from 1 to 8 carbon atoms, $R_{15}$ denotes a hydrogen atom or a linear or branched alkyl radical containing from 1 to 8 carbon atoms, $R_{16}$ denotes a hydrogen atom or an $SO_3H$ group, $R_{17}$ denotes a hydrogen atom or a hydroxyl radical.

Mention may be made, as a specific example of a compound of formula (VI) of: 2-hydroxy4-methoxybenzophenone-5-sulphonic acid (compound of formula (VI) in which $R_{14}$, $R_{16}$ and $R_{17}$ are each hydrogen and $R_{15}$ denotes a methyl radical).

The screening agent containing a sulphonic group can also be a sulphonic derivative of formula (VII) below:

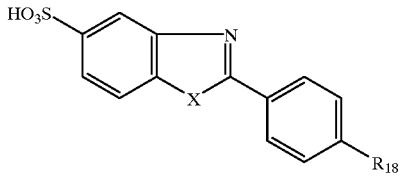

(VII)

in which:

X denotes an oxygen atom or an —NH— radical, $R_{18}$ denotes a hydrogen atom, a linear or branched alkyl or alkoxy radical containing from 1 to 8 carbon atoms or a group of formula (VIII)

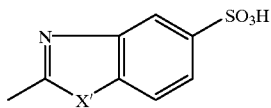

(VIII)

in which X' represents, independently of X, an oxygen atom or an —NH— radical.

As specific examples, mention may be made of the compounds of formula (VII) below, in which:

X denotes an —NH— radical and $R_{18}$ denotes a hydrogen atom: 2-phenylbenzimidazole-5-sulphonic acid.

X denotes an —NH— radical and $R_{18}$ denotes the group of formula (VIII) in which X' denotes an —NH— radical: benzene-1,4-di(benzimidazol-2-yl-5-sulphonic acid).

X denotes an oxygen atom and $R_{18}$ denotes a group of formula (VIII) in which X' denotes an oxygen atom: benzene-1,4-di(benzoxazol-2-yl-5-sulphonic acid).

The compounds of formulae (VI) and (VII) are known compounds which may be prepared according to standard methods described in the prior art.

Examples of screening cosmetic compositions which are preferred in the context of the present invention comprise the following acidic, hydrophilic UV screening agents:

sulphonic derivative of 3-benylidene-2-camphor of formula (I) in which n=0 (1,4-(di(3-methylidenecamphor-10-sulphonic acid))

sulphonic derivative of benzophenone of formula (VI) in which $R_{14}$, $R_{16}$ and $R_{17}$ are each hydrogen and $R_{15}$ denotes a methyl radical (2-hydroxy-4-methoxybenzophenone-5-sulphonic acid, sold in particular by BASF under the name UVINUL MS 40).

sulphonic derivative of benzimidazole of formula (VII) in which X denotes an —NH— radical and $R_{18}$ denotes a hydrogen atom (2-phenylbenzimidazole-5-sulphonic acid, sold in particular by Merck under the name EUSOLEX 232).

The hydrophilic UV screening agent containing at least one sulphonic acid radical is preferably present in the compositions according to the invention at a total concentration of ranging from approximately 0.05 to approximately 10% by weight, and more preferably from approximately 0.25 to approximately 6% by weight, relative to the total weight of the composition.

According to the present invention, the expression "ceramide compound" is understood to refer to ceramides and/or glycoceramides and/or pseudoceramides and/or neoceramides, these being natural or synthetic.

Ceramide compounds are described, for example, in patent applications DE 4,424,530, DE 4,424,533, DE 4,402,929, DE 4,420,736, WO 95/23807, WO 94/07844, EP-A-0646572, WO 95/16665, FR-2,673,179, EP-A-0227994 and WO 94/07844, WO 94124097, WO 94/10131 the disclosures of which are specifically incorporated herein by reference.

The ceramide compounds which can be used according to the present invention preferably correspond to the general formula (IX) below:

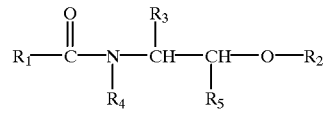

(IX)

in which:

$R_1$ denotes:

a linear or branched, saturated or unsaturated $C_1$–$C_{50}$, preferably $C_5$–$C_{50}$, hydrocarbon radical, it being possible for this radical to be substituted with one or more hydroxyl groups, optionally esterified with an acid $R_7COOH$, wherein $R_7$ is a saturated or unsaturated, linear or branched, optionally mono- or polyhydroxylated $C_1$–$C_{35}$ hydrocarbon radical, it being possible for the hydroxyl(s) of the radical $R_7$ to be esterified with a saturated or unsaturated, linear or branched, optionally mono- or polyhydroxylated $C_1$–$C_{35}$ fatty acid; or a radical R"—(NR—CO)—R', wherein R denotes a hydrogen atom or a mono- or polyhydroxylated, preferably monohydroxylated, $C_1$–$C_{20}$ hydrocarbon radical, and R' and R" are independently hydrocarbon radicals in which the sum of the carbon atoms ranges from 9 to 30, R' being a divalent radical; or a radical $R_8$-O-CO-$(CH_2)_p$, wherein $R_8$ denotes a $C_1$–$C_{20}$ hydrocarbon radical and p is an integer ranging from 1 to 12;

$R_2$ is selected from a hydrogen atom, a saccharide-type radical, in particular a $(glycosyl)_n$, $(galactosyl)_m$ or sulphogalactosyl radical, a sulphate or phosphate residue, a phosphorylethylamine radical and a phosphorylethylammonium radical, in which n is an integer ranging from 1 to 4 and m is an integer ranging from 1 to 8;

$R_3$ denotes a hydrogen atom or a saturated or unsaturated, hydroxylated or non-hydroxylated $C_1$–$C_{33}$ hydrocarbon radical, it being possible for the hydroxyl(s) to be esterified with an inorganic acid or an acid $R_7COOH$, wherein $R_7$ has the same meanings as above, it being possible for the hydroxyl(s) to be etherified with a (glycosyl)$_n$, (galactosyl)$_m$, sulphogalactosyl, phosphorylethylamine or phosphorylethylammonium radical, n and m being defined as above, and it being possible for $R_3$ also to be substituted with one or more $C_1$–$C_{14}$ alkyl radicals; preferably, $R_3$ denotes a $C_{15}$–$C_{26}$ α-hydroxyalkyl radical, the hydroxyl group optionally being esterified with a $C_{16}$–$C_{30}$ α-hydroxy acid;

$R_4$ denotes a hydrogen atom, a methyl or ethyl radical, a saturated or unsaturated, linear or branched, optionally hydroxylated $C_3$–$C_{50}$ hydrocarbon radical or a radical —$CH_2$-$CHOH$-$CH_2$-O-$R_6$ in which $R_6$ denotes a $C_{10}$–$C26$ hydrocarbon radical or a radical $R_8$-O-CO-$(CH_2)_n$, $R_8$ denotes a $C_1$–$C_{20}$ hydrocarbon radical and p is an integer ranging from 1 to 12, $R_5$ denotes a hydrogen atom or a saturated or unsaturated, linear or branched, optionally mono- or polyhydroxylated hydrocarbon radical, it being possible for the hydroxyl(s) to be etherified with a (glycosyl)$_n$, (galactosyl)$_m$, sulphogalactosyl, phosphorylethylamine or phosphorylethylammonium radical, n and m being defined as above, with the proviso that when $R_3$ and $R_5$ denote hydrogen or when $R_3$ denotes hydrogen and $R_5$ denotes methyl, then $R_4$ does not denote a hydrogen atom or a methyl or ethyl radical.

Among the compounds of formula (IX), the preferred ceramides and/or glycoceramides are those whose structure is described by Downing in *Journal of Lipid Research* Vol. 35, 2060–2068, 1994 or those described in French patent application FR-2,673,179, the disclosures of which are specifically incorporated by reference herein.

The ceramide compounds more particularly preferred according to the invention are the compounds of formula (IX) for which $R_1$ denotes a saturated or unsaturated, optionally hydroxylated alkyl derived from $C_{14}$–$C_{22}$ fatty acids; $R_2$ denotes a hydrogen atom; and $R_3$ denotes a linear, optionally hydroxylated $C_{11-17}$ and preferably $C_{13-15}$ radical.

Such compounds are, for example:

2-N-linoleoylaminooctadecane-1,3-diol,

2-N-oleoylaminooctadecane-1,3-diol,

2-N-palmitoylaminooctadecane-1,3-diol,

2-N-stearoylaminooctadecane-1,3-diol,

2-N-behenoylaminooctadecane-1,3-diol,

2-N-[2-hydroxypalmitoyl]aminooctadecane-1,3-diol,

2-N-stearoylaminooctadecane-1,3,4 triol and in particular N-stearoylphytosphingosine, 2-N-palmitoylaminohexadecane-1,3-diol or mixtures of these compounds.

It is also possible to use specific mixtures such as, for example, the mixtures of ceramide(s) 2 and of ceramide(s) 5 according to the Downing classification.

It is also possible to use the compounds of formula (IX) for which $R_1$ denotes a saturated or unsaturated alkyl radical derived from $C_{12}$–$C_{22}$ fatty acids; $R_2$ denotes a galactosyl or sulphogalactosyl radical; and $R_3$ denotes a saturated or unsaturated $C_{12}$–$C_{22}$ hydrocarbon radical and preferably a —CH═CH-$(CH_2)_{12}$—$CH_3$ group.

By way of example, mention may be made of the product consisting of a mixture of glycoceramides, sold under the trade name GLYCOCER by the company Waitaki International Biosciences.

It is also possible to use the compounds of formula (IX) described in patent applications EP-A-0,227,994, EP-A-0,647,617, EP-A-0,736,522 and WO 94/07844, the disclosures of which are specifically incorporated by reference herein.

Such compounds are, for example, QUESTAMIDE H (bis(N-hydroxyethyl-N-cetyl)malonamide, sold by the company Quest, and cetylic acid N-(2-hydroxyethyl)-N-(3-cetyloxy-2-hydroxypropyl)amide.

N-Docosanoyl-N-methyl-D-glucamine, described in PCT patent application WO 94/24097 (the disclosure of which is specifically incorporated by reference herein), can also be used.

The concentration of ceramide compounds can preferably vary from approximately 0.0001% to approximately 20% by weight, relative to the total weight of the composition, and more preferably from approximately 0.001 to approximately 10% and even more preferably from 0.005 to 3% by weight.

The compositions according to the invention can be in the form of a shampoo, a lotion, a gel, an emulsion, a nonionic vesicle dispersion or a lacquer for the hair and can constitute, for example, a rinse-out composition to be applied before or after shampooing, before or after dyeing or bleaching, or before, during or after permanent-waving or straightening the hair, a styling or treating lotion or gel, a blow-drying or hairsetting lotion or gel, or a composition for permanent-waving, straightening, bleaching or dyeing the hair.

These compositions comprise the ingredients usually used in the haircare sector, and can be prepared according to the usual methods known to those skilled in the art.

The compositions can moreover contain conventional cosmetic additives chosen from fatty substances, organic solvents, silicones, thickeners, softeners, surfactants, anionic, cationic, nonionic or amphoteric polymers, anti-foaming agents, hair conditioners such as proteins, vitamins, treating agents (agents for combatting hair loss, antidandruff agents), dyes, fragrances, preserving agents and propellants.

Another subject of the present invention is a process for the cosmetic treatment of the hair intended to protect it against the effects of UV rays, this process consisting in applying to the hair an effective amount of a cosmetic composition as defined above.

Specific, but in no way limiting, examples illustrating the invention will now be given.

EXAMPLE 1

| | |
|---|---|
| - 2-Hydroxy-4-methoxybenzophenone-5-sulphonic acid, sold by the company Rhone Poulenc under the name RHODIALUX S | 0.5 g AM |
| - 2-N-Oleoylaminooctadecane-1,3-diol | 0.5 g |
| - Sodium lauryl ether sulphate containing 2.2 mol of ethylene oxide, as an aqueous solution containing 28% AM | 13.8 g AM |
| - Cocoylbetaine as an aqueous solution containing 30% AM (DEHYTON AB 30 from Henkel) | 2.5 g MA |
| - water qs | 100 g |

The pH was adjusted to 5 with sodium hydroxide.

This shampoo protected the hair against UV radiation and hair washed with this composition was easy to disentangle.

EXAMPLE 2

A rinse-out conditioner of the following composition was prepared:

| | |
|---|---|
| - Benzene-1,4-[di(3-methylidenecamphor- 10-sulphonic acid)] | 1 g AM |
| - 2-N-Oleoylaminooctadecane-1,3-diol | 1 g |
| - Polyacrylamide (SEPIGEL 305 from Seppic) | 2 g AM |
| - Mixture (13/87 by weight) of dimethiconol and cyclomethicone (Q2-1401 from Dow Corning) | 10 g |
| - Preserving agents, fragrance qs | |
| - Water qs | 100 g |

The pH was adjusted to 5 with sodium hydroxide.

This conditioner was applied to washed and towel-dried hair. After leaving to stand on the hair for a certain period, the hair was rinsed with water. The composition protected the hair against UV radiation and hair treated with this composition was soft and easy to disentangle.

EXAMPLE 3

A lotion A of the following composition was prepared:

| | |
|---|---|
| - Benzene-1,4-[di(3-methylidenecamphor-10-sulphonic acid)] as an aqueous solution containing 33% of AM | 0.5 g AM |
| - 2-N-Oleoylaminooctadecane-1,3-diol | 0.5 g |
| - Cocoylbetaine as an aqueous solution containing 30% AM (DEHYTON AB 30 from Henkel) | 3 g AM |
| - Preserving agents qs | |
| - Water qs | 100 g |

The pH was adjusted to 5 with sodium hydroxide.

This lotion was applied to washed and towel-dried hair. After leaving to stand on the hair for a certain period, the hair was rinsed with water. The composition protected the hair against UV radiation and hair treated with this composition was soft and easy to disentangle.

EXAMPLE 4

| | A (Inventive) | B | C |
|---|---|---|---|
| Cocoylbetaine | 3 g AM | 3 g AM | 3 g AM |
| 2-N-Oleoylaminooctadecane-1,3-diol | 0.5 g | | |
| Benzene-1,4-[di(3-methylidene-camphor-10-sulphonic acid)] (UV screening agent) | 0.5 g AM | 0.5 g AM | 1 g AM |
| Preserving agents | qs | | qs |
| Water qs | 100 g | | 100 g |

1 g of each of the compositions A, B and C was applied to 2.5 g locks. After leaving to stand on the locks for 10 min, they were then rinsed with tap water.

A panel of 10 experts was then asked to assess the disentangling ability and the softness of the wet hair.

The 10 experts unanimously preferred the lock treated with composition A according to the invention. Hair treated with composition A disentangled more easily and was softer than hair treated with compositions B or C.

The amount of UV screening agent fixed to hair treated with these three compositions was also compared.

| | A (Invention) | B | C |
|---|---|---|---|
| Conc. of UV screening agent in the composition | 0.5% | 0.5% | 1% |
| Amount of UV screening agent fixed in mg per g of hair | 0.55 | 0.26 | 0.51 |

It was observed that the amount fixed when composition A according to the invention was applied was twice the amount fixed when composition B, containing the same concentration of UV screening agent but not containing any ceramide-type compound, was applied.

We claim:

1. A cosmetic hair composition comprising, in a cosmetically acceptable medium, at least one ceramide compound and at least one agent for screening out ultraviolet radiation, wherein said at least one agent for screening out ultraviolet radiation contains at least one sulphonic acid radical, and wherein said at least one ceramide compound is present in an amount effective to allow an increased amount of said agent for screening out ultraviolet radiation to be applied to the hair.

2. A cosmetic hair composition according to claim 1, wherein said at least one agent for screening out ultraviolet radiation is a 3-benzylidene-2-camphor compound.

3. A cosmetic hair composition according to claim 2, wherein said at least one agent for screening out ultraviolet radiation is a compound of Formula (I)

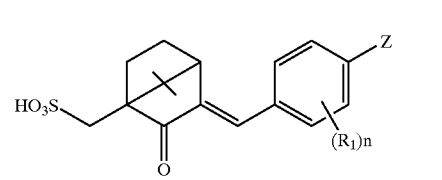

(I)

in which:

Z denotes a group:

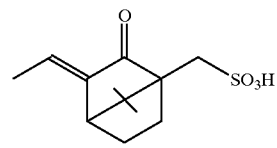

(Z)

n denotes 0 or an integer greater than or equal to 1 and less than or equal to 4, $R^1$ represents at least one, identical or different, linear or branched alkyl or alkoxy radical containing from 1 to 4 carbon atoms;

a compound of Formula (II)

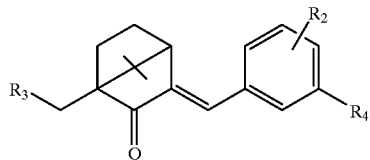

(II)

in which $R_2$ denotes a hydrogen atom, a halogen atom, an alkyl radical containing from 1 to 4 carbon atoms or an —$SO_3H$ radical, $R_3$ and $R_4$ independently denote a hydrogen atom or an —$SO_3H$ radical, and at least one of the radicals $R_2$, $R_3$ and $R_4$ denotes an —$SO_3H$ radical;

a compound of Formula (III)

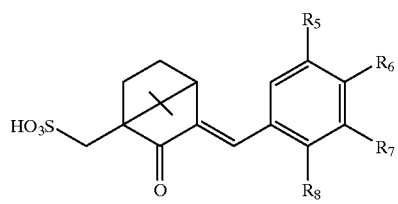

(III)

in which:

$R_5$ and $R_7$ independently denote a hydrogen atom, a hydroxyl radical, a linear or branched alkyl radical containing from 1 to 8 carbon atoms or a linear or a branched alkoxy radical containing from 1 to 8 carbon atoms, wherein at least one of the radicals $R_5$ and $R_7$ represents a hydroxyl, alkyl or alkoxy radical, $R_6$ and $R_8$ independently denote a hydrogen atom or a hydroxyl radical, wherein at least one of the radicals $R_6$ and $R_8$ denotes a hydroxyl radical; a compound of Formula (IV)

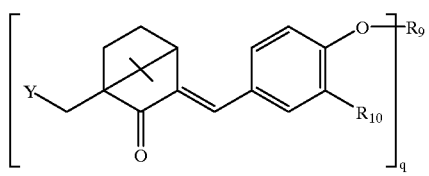

(IV)

in which $R_9$ denotes a hydrogen atom, a linear or branched alkyl radical containing from 1 to 18 carbon atoms, a linear or branched alkenyl radical containing from 3 to 18 carbon atoms, a

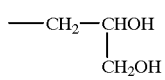

group, a —$(CH_2CH_2O)_n$-H group, a —$CH_2$-CHOH-$CH_3$ group, a —$(CH_2)_m$— group, or a —$CH_2$-CHOH-$CH_2$— group, wherein n is an integer ranging from 1 to 6 and m is an integer ranging from 1 to 10, $R_{10}$ denotes a hydrogen atom, an alkoxy radical containing from 1 to 4 carbon atoms or a divalent radical —O— connected to the radical $R_9$ when $R_9$ is also divalent, q denotes an integer equal to 1 or 2, it being understood that if q is equal to 2, $R_9$ must denote a divalent radical, Y and Y' independently denote a hydrogen atom or an —$SO_3H$ radical, wherein at least one of Y and Y' is an —$SO_3H$ radical; or a compound of Formula (V)

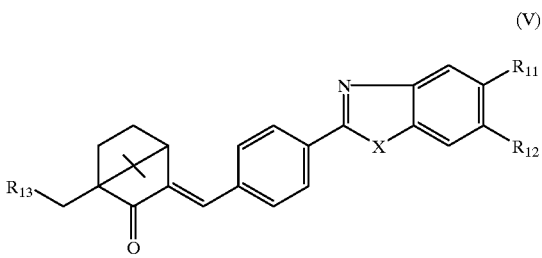

(V)

in which:

$R_{11}$ denotes a hydrogen atom, a linear or branched alkyl or alkoxy radical containing from 1 to 6 carbon atoms or an —$SO_3H$ radical, $R_{12}$ denotes a hydrogen atom or a linear or branched alkyl or alkoxy radical containing from 1 to 6 carbon atoms, $R_{13}$ denotes a hydrogen atom or an —$SO_3H$ radical, wherein at least one of the radicals $R_{11}$ and $R_{13}$ denotes an —$SO_3H$ radical, X is an oxygen or sulphur atom or a group —NR—, wherein R is a hydrogen atom or as linear or branched alkyl radical containing from 1 to 6 carbon atoms.

4. A cosmetic hair composition according to claim 3, wherein said compound of formula (I) is benzene-1,4-[di(3-methylidenecamphor-10-sulphonic acid].

5. A cosmetic hair composition according to claim 3, wherein said compound of formula (II) is a 4-(3-methylidenecamphor)benzenesulphonic acid, a 3-benzylidenecamphor-10-sulphonic acid, a 2-methyl-5-(3-methylidenecamphor)benzenesulphonic acid, a 2-chloro-5-(3-methylidenecamphor)benzenesulphonic acid, or a 3-(4-methyl)benzylidenecamphor-10-sulphonic acid.

6. A cosmetic hair composition according to claim 3, wherein said compound of formula (III) is a (3-t-butyl-2-hydroxy-5-methyl)benzylidenecamphor-10-sulphonic acid, a (3-t-butyl-2-hydroxy-5-methoxy)benzylidenecamphor-10-sulphonic acid, or a (3,5-di-tert-butyl4-hydroxy)benzylidenecamphor-10-sulphonic acid.

7. A cosmetic hair composition according to claim 3, wherein said compound of formula (IV) is a 2-methoxy-5-(3-methylidenecamphor)benzenesulphonic acid, a 3-(4,5-methylenedioxy)benzylidenecamphor-10-sulphonic acid, a 3-(4-methoxy)benzylidenecamphor-10-sulphonic acid, a 3-(4,5-dimethoxy)benzylidenecamphor-10-sulphonic acid, a 3-(4-n-butoxy)benzylidenecamphor-10-sulphonic acid, or a 3-(4-n-butoxy-5-methoxy)-benzylidenecamphor-10-sulphonic acid.

8. A cosmetic hair composition according to claim 3, wherein said compound of formula (1) is 2-[4-(camphormethylidene)phenyl]benzimidazole-5-sulphonic acid.

9. A cosmetic hair composition according to claim 1, wherein said at least one agent for screening out ultraviolet radiation is a compound of formula (VI):

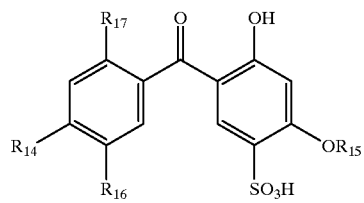

(VI)

in which:
$R_{14}$ denotes a hydrogen atom or a linear or branched alkoxy radical containing from 1 to 8 carbon atoms,
$R_{15}$ denotes a hydrogen atom or a linear or branched alkyl radical containing from 1 to 8 carbon atoms,
$R_{16}$ denotes a hydrogen atom or an $SO_3H$ group, and
$R_{17}$ denotes a hydrogen atom or a hydroxyl radical.

10. A cosmetic hair composition according to claim 9, wherein said compound of formula (VI) is 2-hydroxy4-methoxybenzophenone-5-sulphonic acid.

11. A cosmetic hair composition according to claim 1, wherein said at least one agent for screening out ultraviolet radiation is a compound of formula (VII):

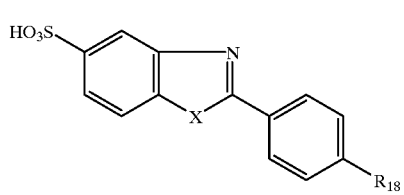

(VII)

in which:
X denotes an oxygen atom or an —NH— radical,
$R_{18}$ denotes a hydrogen atom, a linear or branched alkyl or alkoxy radical containing from 1 to 8 carbon atoms or a group of formula (VIII)

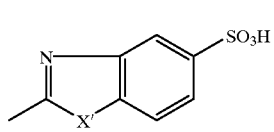

(VIII)

in which X' denotes, independently of X, an oxygen atom or an —NH— radical.

12. A cosmetic hair composition according to claim 11, wherein said compound of formula (VII) is:

a 2-phenylbenzimidazole-5-sulphonic acid, a benzene-1,4-di(benzimidazol-2-yl-5-sulphonic acid, or a benzene-1,4-di(benzoxazol-2-yl-5-sulphonic acid).

13. A cosmetic hair composition according to claim 1, wherein said at least one ceramide compound corresponds to formula (IX):

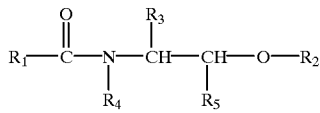

(IX)

in which:

$R_1$ denotes:

a linear or branched, saturated or unsaturated $C_1-C_{50}$ hydrocarbon radical, optionally substituted with one or more hydroxyl groups wherein said one or more hydroxyl groups are optionally esterified with an acid $R_7COOH$, wherein $R_7$ is a saturated or unsaturated, linear or branched, optionally mono- or polyhydroxylated $C_1-C_{35}$ hydrocarbon radical, it being possible for the hydroxyl(s) of the radical $R_7$ to be esterified with a saturated or unsaturated, linear or branched, optionally mono- or polyhydroxylated $C_1-C_{35}$ fatty acid; or a radical R"-(NR-CO)-R', wherein R denotes a hydrogen atom or a mono- or polyhydroxylated $C_1-C_{20}$ hydrocarbon radical, and wherein R' and R" are independently hydrocarbon radicals in which the sum of the carbon atoms ranges from 9 to 30, and R' is a divalent radical; or a radical $R_8$-O-CO-$(CH_2)_p$, wherein $R_8$ denotes a $C_1-C_{20}$ hydrocarbon radical and p is an integer ranging from 1 to 12;

$R_2$ is a hydrogen atom, a saccharide radical, a sulphate residue, a phosphate residue, a phosphorylethylamine radical or a phosphorylethylammonium radical;

$R_3$ denotes a hydrogen atom or a saturated or unsaturated, hydroxylated or non-hydroxylated $C_1-C_{33}$ hydrocarbon radical, it being possible for the hydroxyl(s) to be esterified with an inorganic acid or an acid $R_7COOH$, wherein $R_7$ is a saturated or unsaturated, linear or branched, optionally mono- or polyhydroxylated $C_1-C_{35}$ hydrocarbon radical, it being possible for the hydroxyl(s) to be etherified with a (glycosyl)$_n$, (galactosyl)$_m$, sulphogalactosyl, phosphorylethylamine or phosphorylethylammonium radical, in which n is an integer ranging from 1 to 4 and m is an integer ranging from 1 to 8;

and wherein $R_3$ is optionally substituted with one or more $C_1-C_{14}$ alkyl radicals;

$R_4$ denotes a hydrogen atom, a methyl or ethyl radical, a saturated or unsaturated, linear or branched, optionally hydroxylated $C_3-C_{50}$ hydrocarbon radical or a radical —$CH_2$—CHOH-$CH_2$-O-$R_6$, in which $R_6$ denotes a $C_{10}-C_{26}$ hydrocarbon radical or a radical $R_8$-O-CO-(CH2)p, $R_8$ denotes a $C_1-C_{20}$ hydrocarbon radical and p is an integer ranging from 1 to 12, $R_5$ denotes a hydrogen atom or a saturated or unsaturated, linear or branched, optionally mono- or polyhydroxylated $C_1-C_{30}$ hydrocarbon radical, wherein the hydroxyl(s) are optionally etherified with a (glycosyl)$_n$, (galactosyl)$_m$, sulphogalactosyl, phosphorylethylamine or phosphorylethylammonium radical, in which n is an integer ranging from 1 to 4 and m is an integer ranging from 1 to 8, with the proviso that when $R_3$ and $R_5$ denote hydrogen or when $R_3$ denotes hydrogen and $R_5$ denotes methyl, then $R_4$ does not denote a hydrogen atom or a methyl or ethyl radical.

14. A cosmetic hair composition according to claim 13, wherein $R_1$ denotes a linear or branched, saturated or unsaturated $C_9$–$C_{50}$ hydrocarbon radical, optionally substituted with one or more hydroxyl groups wherein said one or more hydroxyl groups are optionally esterified with an acid $R_7COOH$, wherein $R_7$ is a saturated or unsaturated, linear or branched, optionally mono- or polyhydroxylated $C_1$–$C_{35}$ hydrocarbon radical, it being possible for the hydroxyl(s) of the radical $R_7$ to be esterified with a saturated or unsaturated, linear or branched, optionally mono- or polyhydroxylated $C_1$–$C35$ fatty acid.

15. A cosmetic hair composition according to claim 13, wherein R denotes a monohydroxylated $C_1$–$C_{20}$ hydrocarbon radical.

16. A cosmetic hair composition according to claim 13, wherein said saccharide radical is selected from a (glycosyl)$_n$, (galactosyl)$_m$ or sulphogalactosyl radical, wherein n is an integer ranging from 1 to 4 and m is an integer ranging from 1 to 8.

17. A cosmetic hair composition according to claim 13, wherein $R_3$ denotes a $C_{15}$–$C_{26}$ α-hydroxyalkyl radical, wherein the hydroxyl group is optionally esterified with a $C_{16}$–$C_{30}$ α-hydroxy acid.

18. A cosmetic hair composition according to claim 13, wherein said at least one ceramide compound is a 2-N-linoleoylaminooctadecane-1,3-diol, a 2-N-oleoylaminooctadecane-1,3-diol, a 2-N-palmitoylaminooctadecane-1,3-diol, a 2-N-stearoylaminooctadecane-1,3-diol, a 2-N-behenoylaminooctadecane-1,3-diol, a 2-N-[2-hydroxy-palmitoyl]aminooctadecane-1,3-diol, a 2-N-stearoylaminooctadecane-1,3,4 triol, or a 2-N-palmitoylaminohexadecane-1,3-diol.

19. A cosmetic hair composition according to claim 13, wherein said at least one ceramide compound is N-stearoylphytosphingosine.

20. A cosmetic hair composition according to claim 13, wherein $R_1$ denotes a saturated or unsaturated alkyl radical derived from $C_{12}$–$C_{22}$ fatty acids; $R_2$ denotes a galactosyl or sulphogalactosyl radical; and $R_3$ denotes a saturated or unsaturated $C_{12}$–$C_{22}$ hydrocarbon radical.

21. A cosmetic hair composition according to claim 20, wherein $R_3$ denotes a —CH═CH—(CH$_2$)$_{12}$—CH$_3$ group.

22. A cosmetic hair composition according to claim 13, wherein said at least one ceramide compound is:

a bis-(N-hydroxyethyl-N-cetyl)malonamide, a cetylic acid N-(2-hydroxyethyl)-N-(3-cetyloxy-2-hydroxypropyl)amide, and a N-docosanoyl-N-methyl-D-glucamine.

23. A cosmetic hair composition according to claim 1, wherein said at least one agent for screening out ultraviolet radiation is present in a concentration ranging from 0.05 to 10% by weight, relative to the total weight of the composition.

24. A cosmetic hair composition according to claim 23, wherein said at least one agent for screening out ultraviolet radiation is present in a concentration ranging from 0.25 to 6% by weight, relative to the total weight of the composition.

25. A cosmetic hair composition according to claim 24, wherein said at least one agent for screening out ultraviolet radiation is present in a concentration ranging from 0.1 to 5% by weight, relative to the total weight of the composition.

26. A cosmetic hair composition according to claim 1, wherein said at least one ceramide compound is present in a concentration ranging from 0.0001 to 20% by weight, relative to the total weight of the composition.

27. A cosmetic hair composition according to claim 26, wherein said at least one ceramide compound is present in a concentration ranging from 0.001 to 10% by weight, relative to the total weight of the composition.

28. A cosmetic hair composition according to claim 27, wherein said at least one ceramide compound is present in a concentration ranging from 0.005 to 3% by weight, relative to the total weight of the composition.

29. A process for protecting hair against ultraviolet radiation, said process comprising applying to said hair an effective amount of a cosmetic hair composition according to claim 1.

30. A process for improving the fixing of a hydrophilic ultraviolet screening agent containing at least one sulphonic acid radical to hair, said process comprising incorporating a ceramide compound in a cosmetic hair composition containing said hydrophilic ultraviolet screening agent.

* * * * *

UNITED STATES PATENT AND TRADEMARK OFFICE
CERTIFICATE OF CORRECTION

PATENT NO. : 6,190,676 B1
DATED : February 20, 2001
INVENTOR(S) : Claude Dubief; Daniéle Cauwet-Martin It is certified that error appears in the above-identified patent and that said Letters Patent is hereby corrected as shown below:

Title page,
Item [75], in the Inventors, line 1, "Daniéle" should read -- Danièle --.

Claim 3, column 11,
Line 13, "$R_2$denotes" should read -- $R_2$ denotes --.
Line 16, "$R_3$and" should read -- $R_3$ and --.

Claim 3, column 12,
Line 37, "as linear" should read -- a linear --.

Claim 6, column 12,
Line 58, "butyl14" should read -- butyl-4 --.

Claim 8, column 13,
Line 8, "formula (1)" should read -- formula (V) --.

Claim 10, column 13,
Line 33, "hydroxy4" should read -- hydroxy-4 --.

Claim 13, column 14,
Line 59, "(CH2)p" should read -- $(CH_2)p$ --.

Claim 14, column 15,
Line 7, "$C_9$-$C_{50}$" should read -- $C_5$-$C_{50}$ --.
Line 15, "$C_1$-$C_{35}$"should read $C_1$-$C_{35}$ --.

UNITED STATES PATENT AND TRADEMARK OFFICE
CERTIFICATE OF CORRECTION

PATENT NO. : 6,190,676 B1
DATED : February 20, 2001
INVENTOR(S) : Claude Dubief et al.

It is certified that error appears in the above-identified patent and that said Letters Patent is hereby corrected as shown below:

<u>Claim 16, column 15,</u>
Line 23, "to8" should read -- to 8 --.

Signed and Sealed this

Twenty-fifth Day of September, 2001

*Attest:*

*Attesting Officer*

NICHOLAS P. GODICI
*Acting Director of the United States Patent and Trademark Office*